United States Patent [19]

Doehnert et al.

[11] Patent Number: 4,505,976

[45] Date of Patent: Mar. 19, 1985

[54] STOMA SEAL ADHESIVE

[75] Inventors: Donald F. Doehnert, Millington; Arthur S. Hill, Somerset, both of N.J.

[73] Assignee: Johnson & Johnson Products, Inc., New Brunswick, N.J.

[21] Appl. No.: 486,961

[22] Filed: Apr. 27, 1983

Related U.S. Application Data

[63] Continuation-in-part of Ser. No. 244,194, Feb. 15, 1983, abandoned.

[51] Int. Cl.³ .................... C08K 3/36; C08L 5/04; C08L 5/00; A61L 15/00

[52] U.S. Cl. .................... 428/355; 128/156; 523/111; 523/113; 524/22; 524/45; 524/55; 524/493; 524/503; 524/506; 524/507; 524/521; 524/525; 604/336

[58] Field of Search .................... 128/156; 604/336; 523/111, 113; 524/503, 22, 45, 55; 428/355, 343

[56] References Cited

U.S. PATENT DOCUMENTS

| | | | |
|---|---|---|---|
| 3,339,546 | 9/1967 | Chen | 523/111 |
| 3,511,791 | 5/1970 | Tuckahoe et al. | 523/120 |
| 3,900,633 | 8/1975 | Piron | 428/331 |
| 3,925,271 | 12/1975 | Balinth | 428/355 |
| 4,166,051 | 8/1979 | Cilento et al. | 523/113 |
| 4,177,309 | 12/1979 | Shadbolt | 428/207 |
| 4,253,460 | 3/1981 | Chen et al. | 128/156 |
| 4,296,745 | 10/1981 | Raymond | 128/156 |
| 4,350,785 | 9/1982 | Habib | 523/111 |
| 4,359,047 | 11/1982 | Potaczek | 523/111 |

FOREIGN PATENT DOCUMENTS 17401  10/1980  European Pat. Off. .

OTHER PUBLICATIONS

Derwent Abst. 07457 K/04 (DE 3223147) Jan. 1983.

Primary Examiner—Herbert J. Lilling
Attorney, Agent, or Firm—Wayne R. Eberhardt

[57] ABSTRACT

A pressure-sensitive adhesive having the capacity to absorb at least about 7 percent of its own weight in water and having a desirable combination of plasticity and wet-stick characteristics, as well as good dry skin adhesion. An adhesive composition particularly suitable for use as a stoma seal adhesive comprises (I) from about 30 to about 80 parts by weight each of (a) a pressure-sensitive adhesive component comprising a synthetic or natural gum-like substance and (b) a moisture absorbing component comprising a synthetic carbohydrate or natural water soluble or swellable hydrocolloid together with (II) from about 2 percent to about 20 percent by weight silica, based on the total weight of the adhesive composition.

16 Claims, No Drawings

STOMA SEAL ADHESIVE

This Application is a continuation-in-part of U.S. Pat. No. 244,194, filed 2/15/83, now abandoned.

BACKGROUND OF THE INVENTION

1. Field of the Invention

This invention relates to pressure-sensitive adhesives having the capacity to absorb moisture and therefore adhere to moist body surfaces for a prolonged period of time. More particularly, this invention relates to an improvement in such adhesives which affords them a combination of high plasticity and "wet-stick" adhesion at acceptable levels of moisture absorption over prolonged periods of time, which renders the adhesive particularly suitable for such applications as stoma seal adhesives. This invention also relates to surgical sheet materials such as adhesive tapes and to adhesive bandages and dressings, including plasters that are particularly suitable for use in connection with ostomy appliances as well as for coverings for cuts, abrasions and the like, which comprise a flexible backing member, one of whose major surfaces has adhered thereto a coating of a pressure-sensitive adhesive of the present invention.

Various types of pressure-sensitive adhesives have been proposed and utilized as the adhesive component in adhesive bandages, adhesive tapes and the like. Acrylate polymers, polyolefinic polymers and compounded systems based on natural or synthetic rubber polymers have all been tried or utilized as pressure-sensitive adhesives with varying degrees of success.

A pressure-sensitive adhesive must have certain characteristics to be useful. It must be sufficiently tacky, i.e., have sufficient "grab" or quick-stick," to adhere quickly to the surface to which it is to be adhered. It must also continue to adhere to that surface over extended periods of time. A pressure-sensitive adhesive composition should also have sufficient internal strength to prevent splitting and leaving particles of adhesive on a surface to which an article coated with the adhesive has been adhered when the article is removed. Where the pressure-sensitive adhesive is designed for application to the skin, the problems of adherence are substantially increased. Although the initial tack or stick may be good, adherence over an extended period of time for many pressure-sensitive adhesives requires relatively high shear adhesion to withstand movement of the underlying skin. Also, the adhesive must be tailored to accommodate the nature of the underlying skin surface, as where perspiration and other surface changes may occur. The problem is further complicated by the fact that any pressure-sensitive adhesive designed for application to the skin must release from the skin sufficiently readily to permit removal without skin damage. Where the adhesive is too strongly adhered to the skin and has substantial internal strength, small particles of the upper layer of skin are removed with the adhesive with resulting irritation to the skin. As a result, although many pressure-sensitive adhesives are available for various commercial uses, relatively few have been found which are suitable for articles for skin applications, particular in that many of those having desirable, high sheer adhesion, have an undesirably high resistance to removal, or peel adhesion. This problem is further complicated when the adhesive is intended in such applications as those involving ostomy appliances, where it is required to maintain adhesion for prolonged periods of time while in contact with body fluids, and at the same time to prevent leakage of such fluids therethrough.

A colostomy is the surgical creation of a new opening for the colon on the surface of the body, while an ileostomy is the surgical creation of an opening for the ileum. In an ileostomy the entire colon, the rectum, and sometimes a small portion of the ileum, is removed. In a colostomy the rectum, and sometimes a portion of the colon, is removed.

Both ileostomy and colostomy operations involve the creation of an artificial opening (stoma) in the abdomen to which the distal end of the healthy intestine is attached. Generally, the stoma is placed low on the abdomen and to one side. A related enterostomy for which the stoma seal adhesive of the present invention might be useful is the urinary diversion. It involves the formation of a permanent fistula through which the ureter may discharge its contents.

As a result of the ostomy procedure, means must be provided for conveniently and hygenically collecting human waste material from the resulting stoma. While there are many such ostomy appliances, a common problem experiences with them, as indicated above, is the establishment and maintenance of both good skin adhesion and an adequate seal to prevent waste material coming in contact with the patient's skin. This requires, inter alia, an adhesive material that has good adhesion to both dry and wet skin, adequate moisture absorptivity and sufficient elastic modulus or plasticity to prevent either inadvertent detachment from wet skin or inordinate difficulty or discomfort to the user when the device is intentionally removed.

DESCRIPTION OF THE PRIOR ART

U.S. Pat. No. 3,339,546, issued Sept. 5, 1967, to Chen, discloses an adhesive composition, that is a blend of a water soluble or swellable hydrocolloid admixed with a water insoluble viscous gum-like elastomer binder, that has been found useful for ostomy appliances.

U.S. Pat. No. 3,925,271, issued Dec. 9, 1975, to Balinth, discloses an uncured pressure-sensitive adhesive that does not have moisture absorbing properties comprising an uncured elastomer, a tackifier and at least 14% by weight of silica. The silica is disclosed to provide the adhesive composition with improved tack and holding power at moderately high temperatures, particularly when in contact with metal surfaces. The adhesive is said to be particularly suited to be used on tapes for joining and sealing together sections of metal ventilating ducts, and the electrical insulation of fractional horsepower electrical motors. This patent also refers to U.S. Pat. No. 2,909,278 as disclosing the inclusion of small amounts of silica in a pressure-sensitive adhesive composition comprising an elastomer and a tackifier in order to improve the aging characteristics of pressure-sensitive adhesive tape.

U.S. Pat. No. 4,062,361 describes an ostomy sealing disk comprising a first layer of a hydrocholoid and a second layer of an elastomeric material, the layers being firmly secured to each other. The hydrocholoid may be karaya gum, while the elastomeric material is preferably an oil-containing block copolymer, especially a styrene-isoprene or a styrene-butadiene block copolymer.

U.S. Pat. No. 3,511,791 discloses a denture adhesive based on a acrylamide adhesive including a natural gum and an anticaking agent which may be silicone dioxide.

U.S. Pat. No. 3,926,879 discloses an aqueous sealant composition which swells to from 110 percent to 150 percent of its dry volume when in contact with a liquid. The composition is formulated of a dispersed natural or synthetic rubber elastomeric material, 30 to 75 parts of a tacifying resin, 5 to 20 parts of a thickener, and 30 to 100 parts of a filler which may be silicone dioxide.

British Pat. No. 2,046,774 published Nov. 19, 1980 discloses pressure-sensitive adhesive compositions which comprise a plastic matrix in which is dispersed a gelatinous adhesive composition comprising the reaction product of (a) a polyhydric alcohol and (b) a gelatin, a polysaccharide gum or a vinyl resin. The physical characteristics of the adhesive may be modified by incorporating various other materials such as micronized silica as a viscosity modifier.

U.K. patent application Publication GB 2038661A filed Nov. 20, 1978 as Application No. 7845281 and published July 30, 1980, entitled "Surgical Sealant Composition", is concerned with providing material for effecting a seal around a surgically created stoma. The adhesive sealing composition of the invention described and claimed in this British application comprises 100 parts by weight of a non-biodegradable, tacky polymeric binding agent—such as polyisoprene, polyurethane, silicone or polyisobutylene—preferably polyisobutylene, Vistanex LM/MS by Esso Chemicals being particularly preferred; from 12 to 25 parts by weight of an inert reinforcing filler—the only disclosed examples of suitable material being precipitated or fume silica, a particularly preferred example being Aerosil 200V, a form of fume silica sold by Degussa; and from 5 to 150 parts by weight of a water-activated adhesive thickener—the only disclosed suitable example being a polyacrylamide, preferably that sold by Cyanamid as "Cyanomer P250".

Another recent patent that addresses the problem of providing adequate sealing for ostomy devices and contains a discussion of the prior art at columns 2 and 3 is U.S. Pat. No. 4,231,369, issued Nov. 4, 1980, to Sorensen et al. That patent is directed to the use, as ostomy sealing means, of a shaped, gel-like composition comprising a selected cross-linked elastomer, a hydrocolloid dispersed therein, and a hydrocarbon tackifier.

SUMMARY OF THE INVENTION

We have discovered, quite unexpectedly, that the addition of from about 2 percent to about 20 percent by weight, based on the total weight of the adhesive composition, of silica to a blend of from about 30 to about 80 parts by weight of a pressure-sensitive adhesive component that is a gum-like substance and from about 30 to about 80 parts by weight of a moisture absorbing component that is a water soluble or swellable synthetic hydrocarbon or natural hydrocolloid provides significantly improved plasticity characteristics to the resulting adhesive composition while maintaining good "wet-stick", "dry-stick" and moisture absorption characteristics, thereby providing a highly desirable adhesive for stoma seal and similar uses.

DESCRIPTION OF THE PREFERRED EMBODIMENTS

In general, the pressure-sensitive adhesive compositions of this invention comprise a pressure-sensitive adhesive component selected from the natural and synthetic gum-like substances, including natural and synthetic elastomers, a moisture absorbing component selected from the synthetic carbohydrate and natural water swellable and water soluble hydrocolloids, and silica. Each of the pressure-sensitive adhesive component and the moisture absorbing component is present in the composition of the invention in an amount of from about 30 to about 80 parts by weight, preferably from about 40 to about 60 parts by weight, while the silica is present in an amount of from about 2 to about 20 weight percent, preferably from about 5 to about 12 weight percent, based on the total weight of the adhesive composition.

Generally the silica should be of a sufficiently small particle size to provide a surface area of at least 130 square meters per gram. Particles having an ultimate particle size of less than 0.03 microns are desirable, while those having an ultimate particle size in the range of 0.020 to 0.030 microns are preferred.

As used herein, the term silica is meant to describe a material having a composition which comprises $SiO_2$ as the major component, usually greater than 80%. It is recognized in the art that silica, however obtained, whether from fumed silica, precipitated silica or natural mined silica, will contain various amounts of other metal oxides such as magnesium oxide, together with some water of crystallization, varying amounts of which can be driven off upon ignition. The presence of these impurities does not alter the properties imparted to the adhesive composition in any observable way. However, to insure uniformity of product, the commercially available silica Hi-Sil 233 manufactured by PPG, Pittsburgh, Pa., is preferred.

Suitable natural and synthetic gum-like substances which may be used singly or in admixture as the pressure-sensitive adhesive component in the adhesive compositions of this invention include natural rubber, silicone rubber, acrylonitrile rubber, polyurethane rubber, polyisobutylene, acrylic polymers and other like substances.

Particularly preferred are the polyisobutylenes (such as those supplied commercially by Exxon as Vistanex L100 and Vistanex LM-MH) and acrylic polymers (such as Acrylate QR667 from Rohm & Haas). The gum-like substance acts as a binder for the hydrocolloid particles and, in addition, renders the final bonding composition elastic and pliable.

Suitable synthetic carbohydrate and natural water swellable or soluble hydrocolloids for use, singly or in admixture, as the moisture absorbing component include karaya gum, locust bean gum, sodium acrylate polymers, polyvinylalcohol, powdered pectin, gelatin, carboxymethylcellulose, high molecular weight polyethylene glycol (such as Carbowax 600 from Union Carbide), and other like substances. The formulated adhesive should be capable of absorbing at least 7 percent moisture in a standard moisture absorbency test wherein a weighted sample of the adhesive which has been dried over a dessicant for at least 72 hours, is placed in a chamber at 100° F. and 90 percent relative humidity for seven days, after which the samples are removed and reweighed to determine moisture pickup. Most preferably, the adhesive composition will have the capacity to absorb at least about 15 percent of its own weight in water in this test.

If desired, the pressure-sensitive adhesive compositions of the present invention can include from 0 to about 10% by weight of the usual modifiers, fillers, extenders, tackifiers, antioxidants, stabilizers, plasticizers, and other such ingredients known in the art for inclusion in such compositions. Thus, for example, plasticizers or solvents, such as mineral oil or petrolatum may be added to improve adhesive characteristics and/or to provide the desired consistency. Particularly when the gum-like substance comprises a polyisobutylene, a low molecular weight polybutene (such as Vistac 300 from Exxon) may be included as a tackifier. The extenders can include finely divided clays, bentonites, carbonates such as calcium carbonate, diatomaceous earth, starches or other inert ingredients normally used in adhesive compositions. Antioxidants and stabilizers can be utilized at levels of from about 0.2 percent to about 3 percent by weight of the total composition, preferably from about 1 percent to about 2 percent. Suitable antioxidants and stabilizers include butyl zimate; 2,6,ditert.-butyl-4 methyl phenol, sold under the trademark Ionol by Shell Chemical Company; 2,5-di(-tertamyl)hydroquinone, sold under the trademark Santowar A by Monsanto Chemical Company; a mixture of alkylated diphenyl amines sold under the trademark Agerite Stalite by Vanderbilt Chemical Company, and the like. These stabilizers and antioxidants give improved shelf life characteristics and prevent degradation of the pressure-sensitive adhesive compositions of the present invention.

It has further been found that to obtain pressure-sensitive adhesive compositions with the desired characteristics, it is necessary for such compositions to have a Williams plasticity number of from about 2 mm to about 4 mm, preferably about 2.3 mm to about 2.7 mm as determined according to the procedure of ASTM 0926-67 (1978). If the Williams plasticity number is below 2 mm, the adhesive compositions will be too soft and exhibit undesirable flow, and will have an undesirably high tendency to leave particles of adhesive adhered to the skin upon removal. If the Williams plasticity number is above 4 mm, the adhesive compositions will be too hard and exhibit poor tackiness. The Williams plasticity number of the adhesive composition of the present invention may be increased by the addition of silica to the composition without adversely affecting the other important properties of the adhesive.

Pressure-sensitive adhesive compositions for use as stoma adhesives must also pass a standard wet-stick adhesion test. The procedure for evaluating "wet-stick adhesion" is as follows: A 2 inch square gauze sponge is cut and saturated with a 0.9 percent saline solution contained in a petri dish. The gauze sponge is removed and the excess solution is allowed to drip off for 3 to 4 seconds. The saturated gauze sponge is then placed into a dry petri dish. A 2 inch square sample of a pressure-sensitive adhesive material consisting of a suitable backing covered on one side with the adhesive to be tested is placed upon the saturated gauze sponge and the petri dish is covered. The sample is then checked for adhesion after 5 minutes, 60 minutes, and 24 hours by picking up the adhesive sample and gently shaking it. If the wet sponge sticks to the sample and does not fall off with gentle shaking, the adhesive composition is considered to pass the test for wet-stick.

In addition to the use of the adhesive compositions of this invention by themselves, very satisfactory surgical sheet materials are obtained when a thin, pliable substrate has coated on one side thereof a layer of an adhesive bonding composition of this invention. Suitable substrates which may be employed in the practice of this invention include various papers, woven and nonwoven fabrics, such as cellulose acetate cloth, polymeric films prepared from such materials as polyethylene polymers, polypropylene, copolymers of vinylidene chloride, fluorohalocarbon film, condensation products of ethylene glycol and terephthalic acid, polyamide films and other like flexible sheet materials.

In the preparation of pressure-sensitive surgical sheet materials for application to the skin, such as pressure-sensitive adhesive tapes, adhesive bandages, surgical drapes, and the like, the pressure-sensitive adhesive compositions of the present invention are coated onto a flexible backing material in accordance with known techniques, such as calendering, extrusion, deposition using organic media, and the like.

The film or other substrate which may be employed in the practice of this invention may have a thickness of from 0.0005 inch to 0.05 inch, more preferably from 0.0005 to 0.002 inch. The adhesive composition is applied to a surface of the film in sufficient amount to afford adequate adhesion in use.

EXAMPLES

Specific embodiments of the present invention are illustrated by the following examples. It will be understood, however, that the present invention is not confined to the specific limitations set forth in the individual examples, but rather to the scope of the appended claims.

EXAMPLE 1

A pressure-sensitive adhesive composition was prepared on a two roll laboratory mill at a temperatures of about 240° F. as follows: 510 grams of polyisobutylene were mixed for 10 minutes. Next, 300 grams of carboxymethylcellulose, 200 grams of karaya gum and 100 grams of silica were blended as dry powders and slowly sprinkled onto the mill over about 10 minutes and mixing continued for an additional 15 minutes. 90 grams of liquid polybutene were then slowly poured onto the adhesive and milled until uniform in appearance.

EXAMPLES 2-7

Following the procedure of Example 1, additional pressure-sensitive adhesive compositions illustrative of the present invention were prepared, having the compositions shown in the following table:

| Example No. | 1 | 2 | 3 | 4 | 5 | 6 | 7 |
|---|---|---|---|---|---|---|---|
| Elastomer | | | | | | | |
| Polyisobutylene | 510 | 530 | 200 | — | — | 600 | 510 |
| Acrylate copolymer | — | — | 400 | 600 | 600 | — | — |
| Polybutene | 90 | 70 | — | — | — | — | 70 |
| Hydrocolloid | | | | | | | |
| Carboxymethyl-cellulose | 300 | 180 | 350 | 350 | — | 300 | 300 |
| Karaya Gum | 200 | — | 150 | 150 | — | 200 | — |
| Gelatin | — | 175 | — | — | 100 | — | 100 |
| Pectin | — | 175 | — | — | 100 | — | 100 |
| Silica | 100 | 70 | 100 | 100 | 100 | 100 | 100 |

The adhesive compositions of the foregoing examples were pressed into 4 inch square wafers, 60 mils thick, and tested for wet stick, moisture absorption, plasticity and adhesive properties. All samples passed the standard wet-stick test. Moisture absorption was greater than 7 percent in all cases, and was typically in the range of 14 percent to 18 percent. Williams plasticity numbers for these adhesive compositions were within the acceptable range of 2 mm to 4 mm, and predominantly in the range of 2.1 mm to 2.5 mm. The adhesive properties of the 60 mil wafers, particularly adhesive and cohesive strength, were acceptable for use in ostomy appliances as well as for coverings for cuts, abrasions and the like.

As will be apparent to those skilled in the art, and as indicated above, many modifications and variations of the foregoing detailed description are possible within the spirit and scope of the present invention.

Having thus described our invention, what we desire to secure by Letters Patent is defined in the appended claims.

What is claimed is:

1. A pressure-sensitive adhesive composition having a Williams Plasticity Number of from about 2 mm to 4 mm and the capacity to absorb at least about 7 percent of its own weight in water comprising:
   (a) from about 30 to about 80 parts by weight of a pressure-sensitive adhesive component selected from the group consisting of natural rubber, silicone rubber, acrylonitrile rubber, polyurethane rubber, polyisobutylene, acrylic polymers and mixtures thereof,
   (b) from about 30 to about 80 parts by weight of a moisture absorbing component selected from the group consisting of karaya gum, locust bean gum, sodium acrylate polymers, polyvinylalcohol, powdered pectin, gelatin, carboxymethylcellulose, high molecular weight polyethylene glycol, and mixtures thereof; and
   (c) from about 2 percent to about 20 percent by weight based on the total weight of said adhesive composition of silica.

2. The composition of claim 1 wherein the silica is present in an amount of from about 4 percent to about 12 percent by weight.

3. The composition of claim 1 wherein the adhesive component is selected from polyisobutylene and acrylic polymers.

4. The composition of claim 1 wherein the moisture absorbing component is selected from carboxymethylecellulose, karaya gum, pectin and gelatin.

5. The composition of claim 1 which comprises from about 0 to about 60 parts by weight of each of said adhesive component and said moisture absorbing component.

6. The composition of claim 5 wherein the adhesive component is polyisobutylene and the moisture absorbing component comprises carboxymethylcellulose and karaya gum.

7. The composition of claim 5 wherein the adhesive component is a blend of polyisobutylene and an acrylate copolymer and the moisture absorbing component comprises carboxymethylcellulose, gelatin and pectin.

8. The composition of claim 6 further comprising polybutene.

9. The composition of claim 1 having the capacity to absorb at least about 15 percent of its own weight in water.

10. The composition of claim 1 having a Williams plasticity number of from about 2.1 mm to 2.5 mm.

11. A pressure-sensitive adhesive composition having a Wiliams Plasticity Number of from about 2 mm to 4 mm and the capacity to absorb at least about 7 percent of its own weight in water comprising:
   (a) from about 40 to about 60 parts by weight of a pressure-sensitive adhesive component selected from the group consisting of polyisobutylene and acrylic polymers and mixtures thereof;
   (b) from about 40 to about 60 parts by weight of a moisture absorbing component selected from the group consisting of karaya gum, powdered pectin, gelatin, carboxymethylcellulose and mixtures thereof, and;
   (c) from about 4 percent to about 12 percent by weight based on the total weight of said adhesive composition of silica.

12. The composition of claim 11 further comprising polybutene.

13. The composition of claim 11 having the capacity to absorb from about 14 percent to 18 percent of its own weight in water.

14. The composition of claim 11 having a Williams plasticity number of from about 2.1 mm to 2.5 mm.

15. A pressure-sensitive surgical sheet material comprising a thin pliable substrate bearing on at least one surface thereof the composition of claim 1.

16. A pressure-sensitive surgical sheet material comprising a thin pliable substrate bearing on at least one surface thereof the composition of claim 11.

* * * * *

UNITED STATES PATENT OFFICE
CERTIFICATE OF CORRECTION

Patent No. 4,505,976  Dated March 19, 1985

Inventor(s) Donald F. Doehnert et al.

It is certified that error appears in the above-identified patent and that said Letters Patent are hereby corrected as shown below:

Column 7, line 47 (claim 5)

"about 0 to about 60 parts by weight"

should be

--about 40 to about 60 parts by weight--

Signed and Sealed this

Twenty-sixth Day of November 1985

[SEAL]

Attest:

Attesting Officer

DONALD J. QUIGG

Commissioner of Patents and Trademarks